(12) United States Patent
Boyd et al.

(10) Patent No.: US 12,116,519 B2
(45) Date of Patent: *Oct. 15, 2024

(54) FABRICATION OF LUMINESCENT QUANTUM DOT THIOL-YNE NANOCOMPOSITES WITH TAILORABLE OPTICAL, THERMAL AND MECHANICAL PROPERTIES

(71) Applicant: The Government of the United States of America, as represented by the Secretary of the Navy, Arlington, VA (US)

(72) Inventors: Darryl A. Boyd, Alexandria, VA (US); Michael H. Stewart, Springfield, VA (US); Kimihiro Susumu, Alexandria, VA (US); Eunkeu Oh, Alexandria, VA (US); James P. Wissman, Hyattsville, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 269 days.

This patent is subject to a terminal disclaimer.

(21) Appl. No.: 17/713,983

(22) Filed: Apr. 5, 2022

(65) Prior Publication Data
US 2022/0228061 A1    Jul. 21, 2022

Related U.S. Application Data

(60) Continuation of application No. 17/363,526, filed on Jun. 30, 2021, which is a division of application No.
(Continued)

(51) Int. Cl.
*C09K 11/02* (2006.01)
*C07C 323/60* (2006.01)
(Continued)

(52) U.S. Cl.
CPC .......... *C09K 11/886* (2013.01); *C07C 323/60* (2013.01); *C07D 339/04* (2013.01); *C08F 138/00* (2013.01); *C09K 11/02* (2013.01)

(58) Field of Classification Search
CPC ....... C09K 11/02; C09K 11/025; C09K 11/06; C09K 11/08; C09K 11/886; C07D 339/04
See application file for complete search history.

(56) References Cited

U.S. PATENT DOCUMENTS 11,180,696 B2 *  11/2021  Boyd ................... C07C 323/60

OTHER PUBLICATIONS

La Rosa et al., "An Efficient Method for the Surface Functionalization of Luminescent Quantum Dots with Lipoic Acid Based Ligands", Eur. J. Inorg. Chem., pp. 5143-5151. (Year: 2017).*

(Continued)

*Primary Examiner* — Matthew E. Hoban
*Assistant Examiner* — Lynne Edmondson
(74) *Attorney, Agent, or Firm* — US Naval Research Laboratory; Stephen T. Hunnius

(57) ABSTRACT

This disclosure concerns a method of making a ligand for Quantum Dot functionalization, a method of making a functionalized Quantum Dot (QD) with a ligand, and a method of making a transparent luminescent quantum dot thiol-yne nanocomposite with tailorable optical, thermal, and mechanical properties. The prepolymer solution and functionalized Quantum Dot can be used in additive manufacturing.

11 Claims, 6 Drawing Sheets

Related U.S. Application Data

16/153,357, filed on Oct. 5, 2018, now Pat. No. 11,180,696.

(60) Provisional application No. 62/570,878, filed on Oct. 11, 2017.

(51) Int. Cl.
*C07D 339/04* (2006.01)
*C08F 138/00* (2006.01)
*C09K 11/06* (2006.01)
*C09K 11/08* (2006.01)
*C09K 11/88* (2006.01)

(56) References Cited

OTHER PUBLICATIONS

Stewart et al., "Fabrication of Photoluminescent Quantum Dot Thiol-yne Nanocomposites via Thermal Curing or Photopolymerization", ACS Omega, 3, pp. 3314-3320. (Year: 2018).*

* cited by examiner

FABRICATION OF LUMINESCENT QUANTUM DOT THIOL-YNE NANOCOMPOSITES WITH TAILORABLE OPTICAL, THERMAL AND MECHANICAL PROPERTIES

REFERENCE TO RELATED APPLICATION

This application is a non-provisional of, and claims priority to and the benefits of, U.S. Provisional Patent Application No. 62/570,878 filed on Oct. 11, 2017, and U.S. patent application Ser. No. 16/153,357 filed on Oct. 5, 2018, and U.S. patent application Ser. No. 17/363,526 filed on Jun. 30, 2021, the entirety of each is hereby incorporated by reference.

BACKGROUND

This disclosure teaches the development of polymeric materials, made using thiol-yne chemistry, and having quantum dot nanoparticles incorporated into them to produce transparent, luminescent materials with tailorable mechanical, optical and thermal properties.

These materials may be used as screens in device displays, and/or as materials used in additive manufacturing.

Modern technology comprises numerous ubiquitous devices that utilize visual displays, including mobile phones, flat screen televisions and touch screen car panels. Despite using common, well-studied materials in those displays, there is an earnest search for materials that can improve such devices by using display materials that can simultaneously impart various characteristics such as flexibility, stretchability, durability, scratch resistance, transparency and shatterproof qualities to the display, and consequently to the device it is used in.

There has also been a desire to find materials that have enhanced color characteristics in order to provide displays with brighter and more realistic visual output. Polymers fabricated via thiol-yne chemistry provide a route toward such multifunctional materials, while luminescent quantum dot (QD) nanoparticles can impart improved color properties.

However, to date there have been no reports of combining polymers made using thiol-yne chemistry with QDs that would allow for their use in device displays.

Our invention entails the synthesis of novel ligands (used to functionalize QDs), followed by the incorporation of QDs into a thiol-yne prepolymer matrix, and subsequent polymerization of the material (either by photopolymerization or by thermal curing) to produce luminescent QD thiol-yne nanocomposites.

SUMMARY OF DISCLOSURE

Description

This disclosure teaches the development of polymeric materials, made using thiol-yne chemistry, and having quantum dot nanoparticles incorporated into them to produce transparent, luminescent materials with tailorable mechanical, optical and thermal properties.

These materials may be used as screens in device displays, and/or as materials used in additive manufacturing.

Our invention entails the synthesis of novel ligands (used to functionalize QDs), followed by the incorporation of QDs into a thiol-yne prepolymer matrix, and subsequent polymerization of the material (either by photopolymerization or by thermal curing) to produce luminescent QD thiol-yne nanocomposites.

DESCRIPTION OF THE DRAWINGS

The following description and drawings set forth certain illustrative implementations of the disclosure in detail, which are indicative of several exemplary ways in which the various principles of the disclosure may be carried out. The illustrated examples, however, are not exhaustive of the many possible embodiments of the disclosure. Other objects, advantages and novel features of the disclosure will be set forth in the following detailed description when considered in conjunction with the drawings.

DETAILED DESCRIPTION OF THE INVENTION

This disclosure teaches the development of polymeric materials, made using thiol-yne chemistry, and having quantum dot nanoparticles incorporated into them to produce transparent, luminescent materials with tailorable mechanical, optical and thermal properties.

These materials may be used as screens in device displays, and/or as materials used in additive manufacturing.

Our invention entails the synthesis of novel ligands (used to functionalize QDs), followed by the incorporation of QDs into a thiol-yne prepolymer matrix, and subsequent polymerization of the material (either by photopolymerization or by thermal curing) to produce luminescent QD thiol-yne nanocomposites.

Example 1

Figure 1:
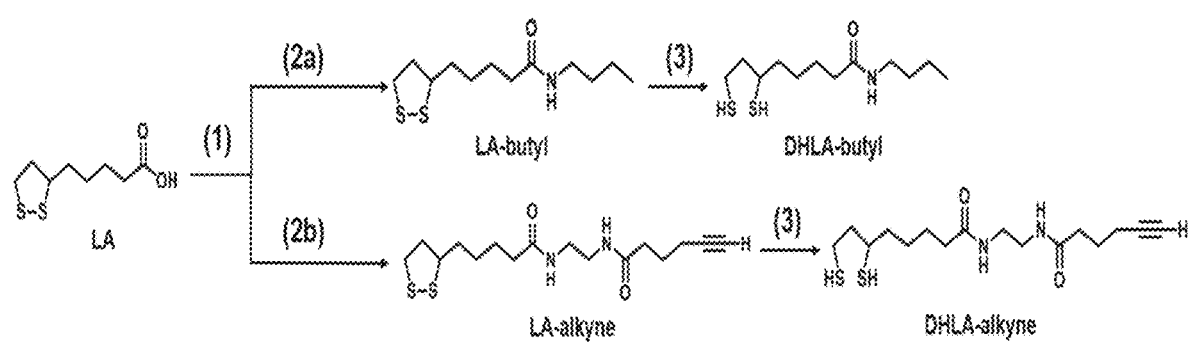
FIG. 1 is an illustration of synthesis of DHLA-butyl and DHLA-alkyne ligands. (1) depicts carbonyldiimidazole, depicts butylamine upper reaction, depicts N-(2-aminoethyl)-5-hexynamide lower reaction, and depicts sodium borohydride prior to product.

In our process, to fabricate luminescent polymer nanocomposites, novel ligands were synthesized to functionalize QDs, as shown in FIG. 1.

Separately, a thiol-yne prepolymer was prepared by combining 1 mole equivalent of the tetrathiol pentaerythritol tetrakis (3-mercaptopropionate) (PETMP) with 1 mole equivalent of the dialkyne 1,7-octadiyne (ODY).

Example 2

Figure 2:
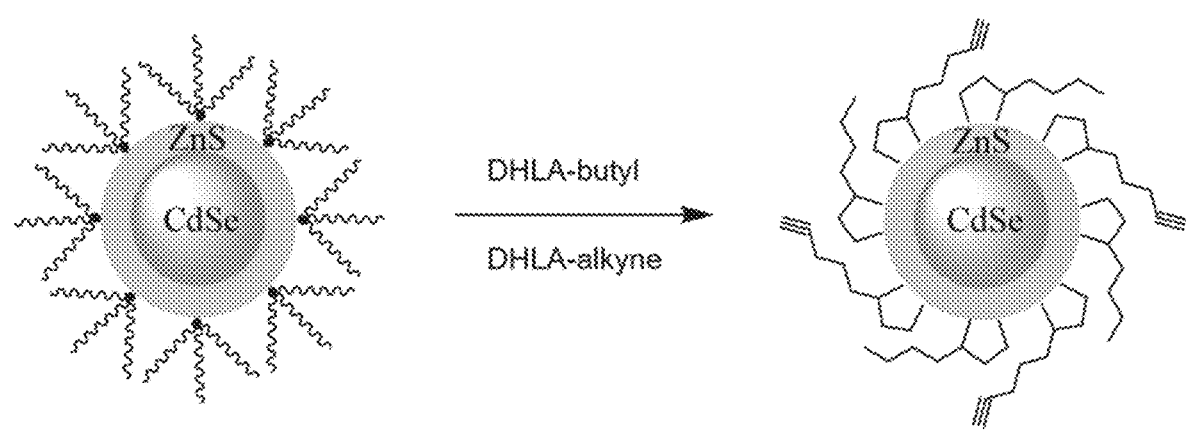
FIG. 2 is a graphic depicting the QDs before and after ligand functionalization.

QD pellets were mixed with a chloroform solution (1-1.5 mL) of DHLA-alkyne (30%) and DHLA-butyl (70%) at an excess of 30,000 ligands per QD, as shown in FIG. 2.

The mixture was sealed under nitrogen and heated overnight at 45° C. with stirring. The QDs were cooled and precipitated from chloroform (using acetonitrile), centrifuged, then dissolved in chloroform and filtered to give functionalized QDs.

The ligands functionalizing the QDs allowed for facile incorporation of the QDs into, and interaction with, the polymer matrix.

Example 3

Functionalized QDs were suspended in a 1.5 µM solution of chloroform. The thiol-yne prepolymer and the QD solution were combined in a glass vial, and the capped vial was mixed by vigorous shaking (~5 seconds) to form a single phase solution, as shown in FIG. 3.

The uncapped vial was then heated (~80° C.) on a hot plate to evaporate away the chloroform solvent.

Upon solvent evaporation, the QD thiol-yne nanocomposite prepolymer was polymerized either by thermal curing (at 80° C. for ~30 mins) or by ultraviolet irradiation (~365 nm for ~10 seconds).

Figure 3:
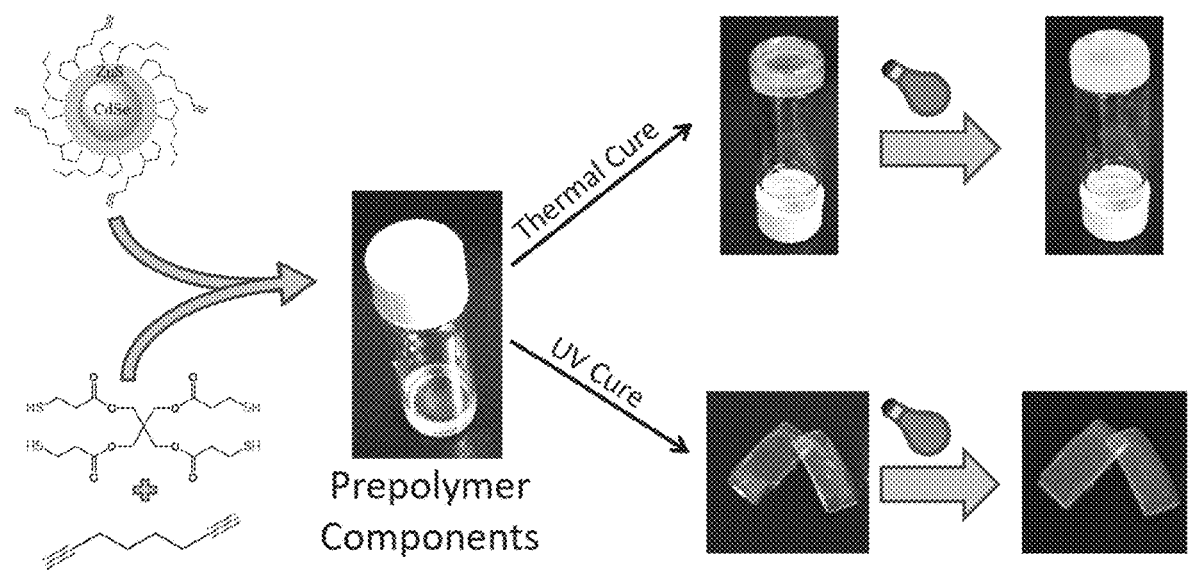
FIG. 3 illustrates the QD thiol-yne nanocomposite fabrication process.

Polymerization by UV irradiation required the addition of less than 1 mol % 2,2-dimethoxy-2-phenylacetophenone (DMPA) photoinitiator, as shown in FIG. 3.

Figure 4:
FIG. 4 is a photograph image of molded thiol-yne polymer containing red QDs in ambient conditions showing transparency (scale bar=1 cm) and a photograph image of molded thiol-yne polymer containing red QDs under UV irradiation. Inset: representative TEM image of red QDs (1.5 uM) within a thiol-yne matrix (inset scale bar=50 nm).

The resulting nanocomposites were transparent, and luminescence within them was revealed by illumination with UV energy, as shown in FIG. 4.

Our process uses polymers made from thiol-yne chemistry as the host material for QDs.

The use of thiol-yne chemistry instead of other similar chemistries is important because thiol-yne chemistry has been shown, by comparison, to have improved mechanical and thermal properties while maintaining high-quality optical properties.

Furthermore, in addition to providing financially cheap processing, unlike many other polymer chemistries, thiol-yne chemistry does not suffer from oxygen inhibition. Specifically utilizing polymers made from thiol-yne chemistry imparts characteristics (e.g. high strength, flexibility, high refractive index) that are unique and possibly inaccessible using other polymer chemistries. The study of thiol-yne chemistry in the modern technology era is relatively new (<10 yrs old), and due to the success of several other materials that have been established for decades (e.g. silica glass, sapphire glass, polyurethanes, polycarbonates), the potential for the use of polymers made from thiol-yne chemistry in technological applications has largely gone unnoticed.

Figure 5:
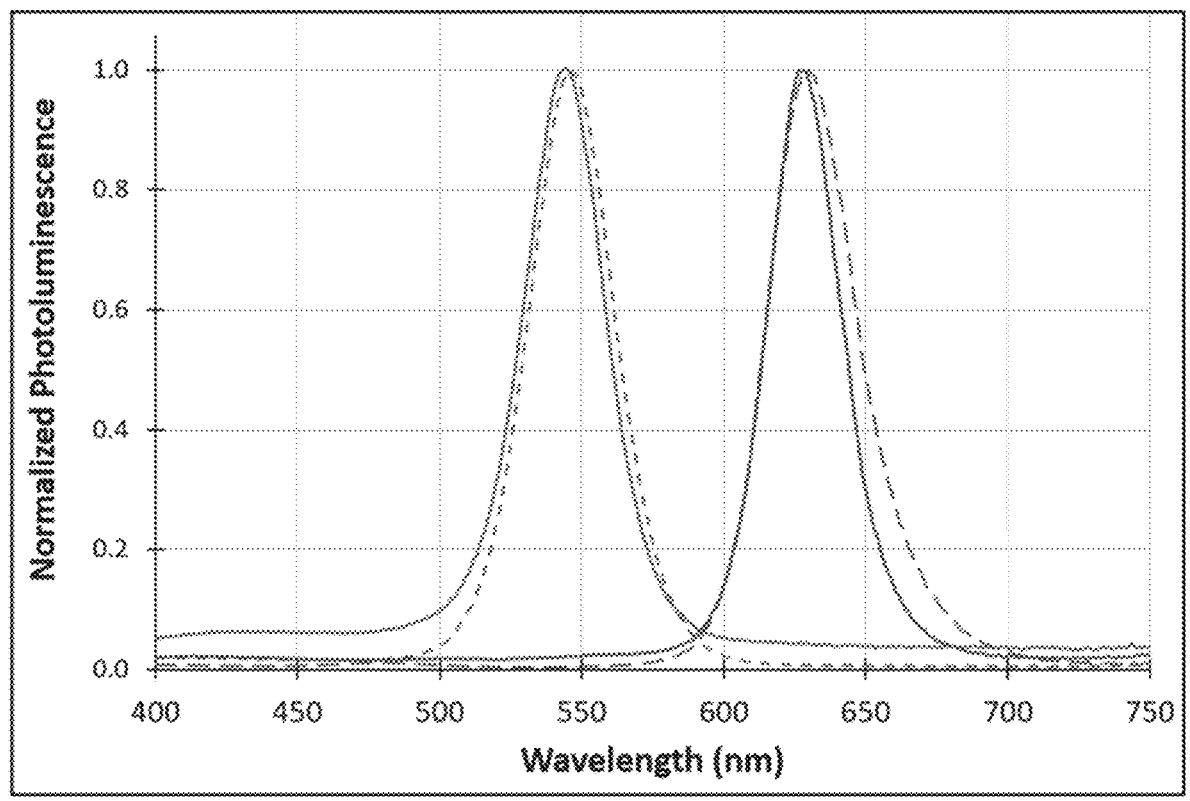
FIG. 5 illustrates photoluminescence (PL) spectra of green QDs in thiol-yne polymer (solid line) versus green QDs in solution (dashed line), and PL spectra of red QDs in thiol-yne polymer (solid line) versus red QDs in solution (dashed line).
Figure 6:
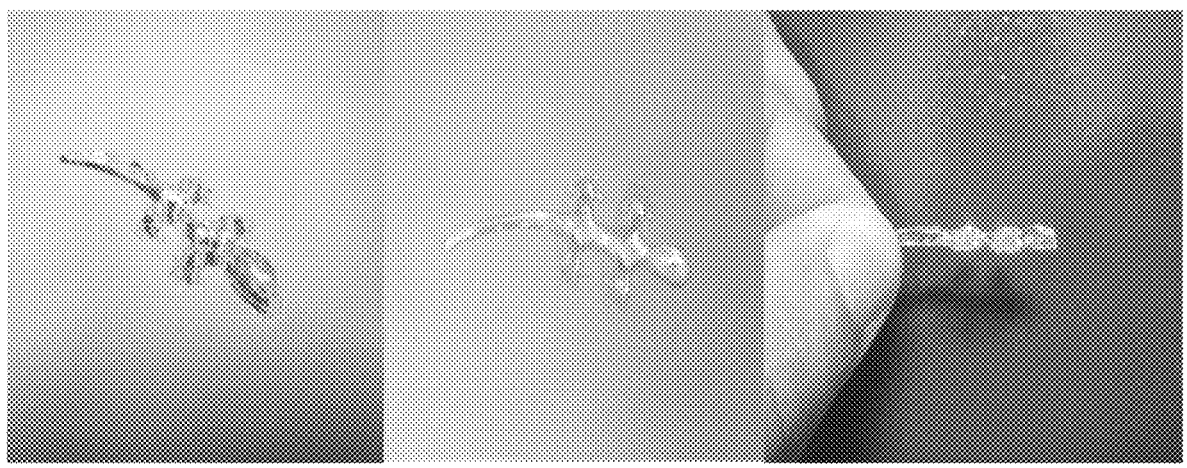
FIG. 6 illustrates images of a gecko fabricated via additive manufacturing using the thiol-yne prepolymer resin.

The use of thiol-yne chemistry is also significant in that nanoparticles, such as QDs, can be incorporated into polymers made using thiol-yne chemistry with little change to the valuable materials properties, as shown in FIG. 5.

Furthermore, incorporating QDs into thiol-yne for use in technological applications has not yet been explored. Consequently, our invention is novel and solves many current problems.

Instead of a polymeric matrix made using thiol-yne chemistry, other related thiol-based chemistries can be used, including but not limited to: thiol-ene chemistry, Thiol-Michael Addition, Thiol-acrylate chemistry, thiol-epoxy chemistry, thiol-norbornene chemistry, Thiol-allyl chemistry, off-stoichiometry thiol-ene chemistry, and/or off-stoichiometry thiol-yne chemistry.

Instead of quantum dot nanoparticles, a variety of other nanoparticles can be used including, but not limited to: metallic nanoparticles, e.g. gold nanoparticles and/or silver nanoparticles, non-metallic nanoparticles e.g. silica nanoparticles and/or clay nanoparticles, and/or anisotropic nanoparticles e.g. nanorods and/or nanocubes.

Instead of a dialkyne monomer, other polyalkynes can be used as part of the prepolymer.

Instead of a tetrathiol monomer, other polythiols can be used as part of the prepolymer.

Instead of thermal polymerization or photopolymerization, other polymerization processes can be used including, but not limited to, radical initiated polymerization.

Instead of the QD nanoparticle functionalization method outlined herein, other methods to functionalize the nanoparticles can be used.

Instead of the ligands outlined herein, other ligands can be used to functionalize the nanoparticles.

Example 4

Synthesis of LA-Butyl

Lipoic acid (0.50 g, 2.4 mmol) and carbonyldiimidazole (0.43 g, 2.7 mmol) were added to a 100 mL round-bottom flask, sealed, and purged with $N_2$. Dry chloroform (15 mL) was added by syringe and stirred for 1 hour. (Scheme 1) The activated lipoic acid mixture was transferred by syringe to an addition funnel and added dropwise to a stirred solution of butylamine (311 µL, 3.1 mmol) in chloroform (15 mL). The reaction mixture was stirred overnight at room temperature under $N_2$. The solvent was removed under vacuum and the residue was chromatographed on silica gel with 15:1 $CHCl_3$:MeOH as the eluent. The fast moving yellow band was collected and the solvent evaporated. The crude product was dissolved in diethyl ether (50-60 mL) and washed with DI water (3×15 mL). The organic layer was dried over $Na_2SO_4$, filtered, and evaporated; this yielded the product (531 mg, 84%) as a yellow residue. TLC $R_f$=0.67, $CHCl_3$:MeOH=10:1 (v/v). $^1$H NMR (400 MHz, $CDCl_3$): 5.40 (s, 1H), 3.57 (m, 1H), 3.25 (m, 2H), 3.08-3.22 (m, 2H), 2.46 (m, 1H), 2.17 (m, 2H), 1.91 (m, 1H), 1.6-1.78 (m, 4H), 1.40-1.56 (m, 4H), 1.30-1.40 (m, 2H), 0.93 (t, 3H, J=7.4 Hz).

Example 5

Synthesis of DHLA-Butyl

LA-butyl (0.380 g, 1.45 mmol) was dissolved in ethanol (20 mL) and DI water (5 mL) and purged with $N_2$. Sodium borohydride (0.165 g, 4.36 mmol) was added and the mixture was stirred for 2 hours. (Scheme 1) The ethanol was removed under reduced pressure and then brine (100 mL) was added. The aqueous solution was extracted with chloroform (3×15 mL). The organic phase was dried over $Na_2SO_4$, filtered, and evaporated to afford the product (0.353 g, 92%) as an oil. $^1$H NMR (400 MHz, $CDCl_3$): 5.37 (s, 1H), 3.25 (m, 2H), 2.92 (m, 1H), 2.60-2.80 (m, 2H), 2.17 (m, 2H), 1.86-1.96 (m, 1H), 1.28-1.80 (m, 11H), 1.25 (t, 1H, J=7.0 Hz), 1.19 (d, 1H, J=6.2 Hz), 0.93 (t, 3H, J=7.4 Hz).

Example 6

Synthesis of N-(2-aminoethyl)-5-hexynamide

N-(2-aminoethyl)-5-hexynamide was synthesized as previously described,[8] with slight modification. Briefly, 5-hexynoic acid (0.50 g, 4.5 mmol) and carbonyldiimidazole (0.80 g, 4.9 mmol) were added to a 100 mL round-bottom flask, sealed, and purged with $N_2$. Dry chloroform (25 mL) was added by syringe and stirred for 1 hour. The activated 5-hexynoic acid mixture was transferred by syringe to an addition funnel and added dropwise to a stirred solution of tert-butyl N-(2-aminoethyl)carbamate (0.72 g, 4.5 mmol) in chloroform (20 mL). The reaction mixture was stirred overnight at room temperature under $N_2$. The solvent was removed under vacuum and diethyl ether (30 mL) and DI water (20 mL) was added to the residue and stirred. The mixture was transferred to a separatory funnel and the organic phase was separated. The aqueous phase was extracted with diethyl ether two more times. The organic phases were combined, dried over $Na_2SO_4$, filtered, and evaporated. The crude residue was chromatographed on silica gel with 15:1 $CHCl_3$:MeOH as the eluent to afford product (0.715 g, 63%) as a solid. $^1$H NMR (400 MHz, $CDCl_3$): 6.13 (s, 1H), 4.87 (s, 1H), 3.36 (m, 2H), 3.27 (m, 2H), 2.32 (t, 2H, J=7.4 Hz), 2.25 (td, 2H, J=6.7, 2.4 Hz), 1.97 (t, 1H, J=2.7 Hz), 1.86 (quint, 2H, J=7 Hz), 1.45 (s, 9H). The Boc-group was removed with trifluoroacetic acid as previously described[9] to yield N-(2-aminoethyl)-5-hexynamide (TFA salt).

Example 7

Synthesis of LA-Alkyne

Lipoic acid (0.579 g, 2.81 mmol) and carbonyldiimidazole (0.50 g, 3.1 mmol) were added to a 100 mL round-bottom flask, sealed, and purged with $N_2$. (Scheme 1) Dry chloroform (20 mL) was added by syringe and stirred for 1 hour. The activated lipoic acid mixture was transferred by syringe to an addition funnel and added dropwise to a stirred solution of N-(2-aminoethyl)-5-hexynamide (TFA salt) (0.753 g, 2.81 mmol) and triethylamine (0.78 mL, 5.6 mmol) in chloroform (30 mL). The reaction mixture was stirred overnight at room temperature under $N_2$. The solvent was removed under reduced pressure. The residue was dissolved in ethyl acetate (50 mL) and washed with 0.1 M $K_2CO_3$ (2×20 mL). The organic phase was dried over $Na_2SO_4$, filtered, and evaporated to dryness. The residue was dissolved in minimal 15:1 $CHCl_3$:MeOH, filtered, and chromatographed on silica gel with 15:1 $CHCl_3$:MeOH yielding the product as a pale-yellow waxy residue (0.588 g, 58%). $^1$H NMR (400 MHz, $CDCl_3$): 6.15 (s, 2H), 3.57 (m, 1H), 3.4 (m, 4H), 3.08-3.20 (m, 2H), 2.48 (m, 1H), 2.33 (t, 2H, J=7.4 Hz), 2.25 (td, 2H, J=6.7, 2.7 Hz), 2.20 (t, 2H, J=7.4 Hz), 1.98 (t, 1H, J=2.7 Hz), 1.82-1.96 (m, 4H), 1.61-1.75 (m, 4H), 1.41-1.53 (m, 2H).

Example 8

Synthesis of DHLA-alkyne

LA-alkyne (0.588 g, 1.63 mmol) was dissolved in THF (15 mL) in a 100 mL round-bottom flask. DI water (5 mL) was added and the mixture was purged with $N_2$. Sodium borohydride (0.185 g, 4.89 mmol) was added to the LA-alkyne solution and stirred for 4 hours. (Scheme 1) The THF was removed under reduced pressure and then chloroform (20 mL) was added followed by brine (60 mL). The mixture was transferred to a separatory funnel and the organic phase was separated. The aqueous phase was extracted with chloroform two more times. The organic phases were combined, dried over $Na_2SO_4$, filtered, and then evaporated to dryness. This afforded the product (0.523 g, 88%) as a white solid. $^1$H NMR (400 MHz, $CDCl_3$): 6.15 (s, 2H), 3.40 (m, 4H), 2.92 (m, 1H), 2.70 (m, 2H), 2.33 (t, 2H, J=7.5 Hz), 2.26 (td, 2H, J=6.9, 2.7 Hz), 2.20 (t, 2H, J=7.4 Hz), 1.98 (t, 1H, J=2.5 Hz), 1.81-1.86 (m, 4), 1.38-1.81 (m, 6H), 1.36 (t, 1H, J=7.8 Hz) 1.30 (d, 1H, J=7.9 Hz)

There are several advantages and new features with our invention as disclosed herein.

The disclosed invention creates novel ligands for the functionalization of nanoparticles.

This invention creates a material that can be fabricated by thermal polymerization or photopolymerization.

Our invention creates a material with tailorable optical properties, which are dependent on the monomers used in the prepolymer formulation and/or dependent on the QDs incorporated into the prepolymer.

The disclosed invention creates a material with tailorable mechanical properties, which are dependent on the monomers used in the prepolymer formulation and/or dependent on the QDs incorporated into the prepolymer.

Our invention creates a material with tailorable thermal properties, which are dependent on the monomers used in the prepolymer formulation and/or dependent on the QDs incorporated into the prepolymer.

The above examples are merely illustrative of several possible embodiments of various aspects of the present disclosure, wherein equivalent alterations and/or modifications will occur to others skilled in the art upon reading and understanding this specification and the annexed drawings. In addition, although a particular feature of the disclosure may have been illustrated and/or described with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

What we claim is:

1. A method of making a ligand for Quantum Dot functionalization, comprising the steps of:
    mixing lipoic acid (LA) and carbonyldiimidazole to form a first mixture;
    adding chloroform to the first mixture to form a second mixture;
    adding the second mixture to butylamine in chloroform to form LA-butyl;
    mixing the LA-butyl with sodium borohydride; and
    forming a DHLA-butyl ligand.

2. The method of making a ligand for Quantum Dot functionalization of claim 1, further comprising the steps of:
    incorporating the DHLA-butyl ligand on quantum dots.

3. The method of making a ligand for Quantum Dot functionalization of claim 2, further comprising the steps of:
    incorporating the DHLA-butyl ligand on quantum dots into a polymer.

4. The method of making a ligand for Quantum Dot functionalization of claim 2, further comprising the steps of:
    processing the DHLA-butyl ligand on quantum dots in an organic solvent.

5. The method of making a ligand for Quantum Dot functionalization of claim 1
    wherein the DHLA-butyl ligand comprises a neutral, nonreactive group; further comprising the steps of:
    utilizing the DHLA-butyl ligand to tune surface reactivity of a quantum dot.

6. A product of a process of making a ligand for Quantum Dot functionalization, comprising the steps of:
    mixing lipoic acid (LA) and carbonyldiimidazole to form a first mixture;
    adding chloroform to the first mixture to form a second mixture;

adding the second mixture to butylamine in chloroform to form LA-butyl;
mixing the LA-butyl with sodium borohydride; and
forming a DHLA-butyl ligand.

7. The product of a process of making a ligand for Quantum Dot functionalization of claim 6 wherein
the DHLA-butyl ligand is inert.

8. The product of a process of making a ligand for Quantum Dot functionalization of claim 7 wherein
the DHLA-butyl ligand is hydrophobic.

9. The product of a process of making a ligand for Quantum Dot functionalization of claim 8 wherein
the DHLA-butyl ligand is not charged.

10. The product of a process of making a ligand for Quantum Dot functionalization of claim 9 wherein
the DHLA-butyl ligand promotes miscibility with a polymer monomer.

11. The product of a process of making a ligand for Quantum Dot functionalization of claim 10 wherein
the DHLA-butyl ligand acts as a neutral, nonreactive group to tune surface reactivity.

* * * * *